United States Patent [19]
Kronish et al.

[11] 3,957,584
[45] May 18, 1976

[54] DETECTION OF BETA-GALACTOSIDASE PRODUCING MICRO-ORGANISMS

[75] Inventors: Donald P. Kronish, Rockaway; William D. Young, Montclair, both of N.J.

[73] Assignee: Warner-Lambert Company, Morris Plains, N.J.

[22] Filed: Sept. 30, 1974

[21] Appl. No.: 510,816

[52] U.S. Cl. .......................... 195/103.5 R; 195/100; 195/102
[51] Int. Cl.² ...................... C12K 1/04; C12K 1/10
[58] Field of Search .............. 195/103.5 C, 103.5 R, 195/99–102; 23/253 TP

[56] References Cited
UNITED STATES PATENTS

| | | | |
|---|---|---|---|
| 3,359,180 | 12/1967 | Evans et al. | 195/103.5 R |
| 3,645,853 | 2/1972 | Kronish et al. | 195/103.5 R |
| 3,649,461 | 3/1972 | Evans et al. | 195/103.5 R |
| 3,785,929 | 1/1974 | Kronish et al. | 195/103.5 R |
| 3,870,601 | 3/1975 | Warren et al. | 195/103.5 R |

OTHER PUBLICATIONS

Rosen; R., "Evaluation of the Pathotec 'Rapid I–D System' and Two Additional Experimental Reagent-Impregnated Paper Strips," Applied Microbiology, 26(6):pp. 890–893, Dec. 1973.

Primary Examiner—David M. Naff
Assistant Examiner—C. A. Fan
Attorney, Agent, or Firm—Albert H. Graddis; Frank S. Chow; Anne M. Kelly

[57] ABSTRACT

A diagnostic test system for detecting $\beta$-galactosidase producing micro-organisms is prepared by impregnating one zone of a bibulous material with an aqueous acetone solution of an o-nitrophenyl-$\beta$-D-galactopyranoside substrate and evaporating to dryness; and impregnating a contiguous and separate zone of the bibulous material with a solution of a microbiologically inert buffer system which will maintain a pH of from about 6.5 to 8.5 and evaporating to dryness. Preferably, the bibulous material contains 1.5 mg of dry o-nitrophenyl-$\beta$-D-galactopyranoside and 0.02 millimoles of a buffer which will maintain a pH of 7.4. Optionally, a waterproof barrier zone and an identifying dye zone may be present. In use, the impregnated bibulous material is inserted into a test tube of a saline suspension of unknown organism and incubated for 4 hours. The development of a yellow coloration indicates that $\beta$-galactosidase is produced by the organism being tested. The diagnostic test system of this invention is stable for 1 year at 4°C., at room temperature, and at 37°C.

17 Claims, No Drawings

DETECTION OF BETA-GALACTOSIDASE PRODUCING MICRO-ORGANISMS

BACKGROUND OF THE INVENTION

Although many biochemical tests are available for identifying micro-organisms in the Enterobacteriaceae family, differentiation of organisms such as Arizona or Citrobacter from Salmonella, and *Pseudomonas cepacia* or *P. maltophilia* from other pseudomonads has always been difficult. Recently, the o-nitrophenyl-$\beta$-D-galactopyranoside test has proven useful in differentiating the above-mentioned organisms. This test detects $\beta$-galactosidase-producing organisms by the bacterial hydrolysis of the substrate, o-nitrophenyl-$\beta$-D-galactopyranoside. This last mentioned o-nitrophenyl-$\beta$-D-galactopyranoside, commonly known as "ONPG, is an artificial substrate which is initially colorless in solution. Hydrolysis of the substrate by bacterially-produced $\beta$-galactosidase enzyme, releases free o-nitrophenol, which is yellow under alkaline conditions. Thus, a convenient method for detecting $\beta$-galactosidase activity and the micro-organisms which produce this enzyme, is provided.

The ONPG test has been the subject of a number of studies: Lederberg, J.,J. Bact. 60: 381–392 (1950); Lowe, G.H., J. Med. Technol. 19: 21–25 (1962); Pickett, M.J. et al., Appl. Microbiol. 14: 178–182 (1966); and Sonnenwirth, A.C., Chapter 62, Gradwohl's Clinical Laboratory Methods and Diagnosis, 7th Ed., 1970, pages 1111–1112. In all of the above studies, the ONPG substrate is prepared in a buffer solution at the time the test with an unknown organism is to be run. Pre-prepared substrate solutions of suitable sensitivity and stability have not been reported. Comparative studies on the use of an ONPG diagnostic test strip are reported by Rosner, R. in Appl. Microbiol. 26: 890–893 (December 1973). Results with the ONPG test strip were favorable, according to the Rosner studies, but neither the composition, configuration or method of preparing the test strip are disclosed in this paper. The ONPG test strip used in the Rosner studies is, in fact, an early attempt by the inventors of the diagnostic test system of this invention to prepare a stable, sensitive, product which would accurately detect $\beta$-galactosidase-producing organisms. Unfortunately, the stability of the ONPG test strip studied by Rosner was so short-lived that neither sensitivity of the test product nor the accuracy of the results could be guaranteed should commercial development be undertaken. A pre-prepared diagnostic test system must be able to withstand the manufacturing, shipping and storage conditions normally encountered to be considered suitable for marketing. Such a product must provide reliable, reproducible test results. Thus, while some progress has been made, there is still a need for a pre-prepared, stable, sensitive ONPG test system which can be used for the rapid identification of micro-organisms which produce $\beta$-galactosidase enzymes.

SUMMARY OF THE INVENTION

A diagnostic test system for detecting $\beta$-galactosidase producing organisms, and a method for preparing this test system are provided. From 0.5% to 5.0% weight/volume of an o-nitrophenyl-$\beta$-D-galactopyranoside substrate is dissolved in a 25% to 75% by volume aqueous-acetone solution and applied to one zone of a bibulous carrier material; from 0.5 molar to 1 molar buffer solution which will maintain a pH of 6.5 to 8.5 is applied to a zone of the bibulous carrier material contiguous to the substrate zone. The impregnated, dry bibulous carrier material contains from 0.5 mg to 3.0 mg of the o-nitrophenyl-$\beta$-D-galactopyranoside in one zone and from 0.01 to 0.1 millimoles of buffer in a contiguous zone. Preferably, a mono-basic potassium and dibasic sodium phosphate buffer is used. Optionally, a waterproof barrier zone may be contiguous to the outer-most reagent impregnated zone. In use, the impregnated bibulous carrier material is inserted into a saline suspension of an unknown organism and incubated for four hours; the development of a yellow coloration indicates that a $\beta$-galactosidase-producing orgainism is present. The diagnostic test system of this invention is stable for one year at 4°C., at room temperature and at 37°C.

DESCRIPTION OF THE PREFERRED EMBODIMENTS

It has now been found that a buffered o-nitrophenyl-$\beta$-D-galactopyranoside test system for detecting $\beta$-galactosidase-producing bacteria can be applied to a bibulous carrier material to provide a stable, sensitive test system which can be used for the rapid identification of such micro-organisms. According to the teachings of this invention, an o-nitrophenyl-$\beta$-D-galactopyranoside substrate material is dissolved in a specific concentration of acetone and water and applied to one zone of a bibulous carrier material. The o-nitrophenyl-$\beta$-D-galactopyranoside is an artificial substrate material commercially available from Calbiochem. Co., La Jolla, California, and is commonly known as "ONPG". The solution used for the application of ONPG substrate to the bibulous carrier material is prepared by dissolving from 0.5% to 5.0% weight/volume of ONPG, based on the volume of the total solution, in a solution containing from 25% to 75% by volume of acetone in water. Preferably, the aqueous substrate solution contains 5.0% weight/volume of ONPG and 70% by Volume of acetone. The substrate solution is applied to one extremity of the bibulous carrier material and evaporated to dryness so as to provide from 0.5 mg to 3.0 mg of dry ONPG on one test unit of the bibulous carrier material. The substrate solution may be applied to the bibulous carrier material by any suitable means, on one or both sides of a substrate zone, to obtain the above-mentioned amount of dry ONPG substrate deposited in the substrate zone. Preferably, the ONPG substrate solution is applied 3 times to each side of the bibulous material, to obtain a total of about 1.5 mg of dry substrate on one test unit.

A microbiologically inert buffer system which has the capacity to maintain a pH of from 6.5 to 8.5, preferably 7.2 to 7.6, most preferably 7.4, is applied to a separate but contiguous portion of the bibulous carrier material and evaporated to dryness. Suitable buffer systems which have the above described capacity include: barbital sodium/hydrochloric acid; sodium acetate and barbital sodium/hydrochloric acid; borax/monobasic potassium phosphate; citric acid, phosphoric acid, orthoboric acid and sodium hydroxide/hydrochloric acid; citric acid and dibasic sodium phosphate; monobasic potassium phosphate/dibasic sodium phosphate; piperazine dihydrochloride/sodium hydroxide; piperazine dihydrochloride in glycylglycine/sodium hydroxide; tris[hydroxymethyl]aminomethane/hydrochloric acid; and tris[hydroxymethyl]aminomethane and maleic acid or maleic anhydride/sodium hydroxide. Among the suitable buffer systems, the following are preferred: monobasic potassium phosphate/dibasic sodium phosphate; tris[hydroxymethyl] aminomethane/hydrochloric acid; and barbital sodium/hydrochloric acid. Of these, the monobasic potassium phosphate/dibasic sodium phosphate buffer is a particularly preferred buffer system.

In preparing the solution of buffer system for application to the bibulous carrier material, it has been found that a buffer solution at a concentration of from 0.5 to about 1 molar is suitable. Such solutions are used to deposit the required 0.01 to 0.1 millimoles of buffer on one test unit of bibulous carrier material in a zone separate from but contiguous to, the substrate impregnated zone. In the preferred embodiment of this invention, a 1 molar monobasic potassium phosphate and dibasic sodium phosphate buffer solution is applied to the bibulous carrier material, in a zone contiguous to the substrate zone, to deposit 0.02 millimoles of buffer on one test unit of the bibulous material. As with the application of the substrate solution above, any suitable means for applying the buffer solution to the bibulous carrier material may be used provided the above mentioned amount of dry buffer is deposited in the appropriate zone of the bibulous carrier material. Preferably, the buffer solution is applied twice to each side of the appropriate zone of the bibulous carrier material, with drying between each application.

The above stated amounts of dry substrate and buffer impregnated on the separate but contiguous zones of one test unit of the bibulous carrier material are designed for incubation with approximately 0.3 ml of saline suspension of test organisms for 4 hours at approximately 35°C–37°C. For optimum results within the recommended incubation time, a sufficient amount of test organisms should be present so that the suspension is visibly turbid. A less dense suspension may be used, but would require increased incubation time. A more dense suspension, containing a greater concentration of organisms, can be used with the diagnostic test system of this invention without difficulty. Should the amount of test organism or incubation time or temperature be varied, corresponding adjustments in the amounts of buffer and substrate would be required to insure that sufficient contact between the test reagents and the test organisms has taken place in order to prevent false negative results. The quantities used in the diagnostic test system of this invention have been found to yield accurate, sensitive results as rapidly as possible. Variations in amounts of reagents, amounts of test organisms or incubation time or temperature may, of course, be made but the test system may not be as sensitive or as accurate and results may not be obtained in as short a period of time.

The diagnostic test system of this invention may comprise a bibulous carrier material having only two zones, fully impregnated with substrate and buffer. However, where additional unimpregnated bibulous carrier material is present, application of a waterproof or hydrophobic barrier solution is necessary to prevent migration of the test reagents and end products onto the unimpregnated areas of the bibulous carrier during incubation with the suspension of test organisms. If test reagents become dispersed over the unimpregnated areas of the bibulous carrier material, concentrations actually in contact with test organisms are diminished and results may be inaccurate. Additionally, a positive test result, if pale yellow, may be very difficult to recognize. Therefore, a waterproof or hydrophobic barrier zone is necessary to prevent migration of reagents.

The barrier composition to be applied to the bibulous carrier material must be chemically inert in the biological test system of this invention. Any inert substance which will form a waterproof barrier of this type may be used. Suitable materials include waxes, laquers, and plastics. One such material is the colorless, polymerized methyl methacrylate coating composition marketed by Krylon, Inc., Norristown, Pa., under the trade name Krylon 150 Crystal Clear, which is supplied in a toluene vehicle and may be diluted with additional toluene or diluents such as methyl, ethyl and propyl alcohol. Another suitable barrier composition is a chrome complex marketed under the trade name Quilon by E. I. du Pont de Nemours & Co., Inc., Wilmington, Del., and supplied in an isopropanol solution which may be diluted. A particularly preferred waterproof barrier is obtained by first applying the Quilon coating to the bibulous carrier material and then applying the Krylon 150 Crystal Clear coating over the Quilon coating, with or without drying as described in U.S. Application Ser. No. 292,701, filed Sept. 27, 1972, now U.S. Pat. No. 3,846,247 published Nov. 5, 1974. The above-mentioned barrier coating compositions are applied to both sides of the bibulous carrier material in order to insure complete penetration into the bibulous material.

Optionally, an identification zone for handling the diagnostic test material may be present on the extremity opposite the reagent impregnated zones of the bibulous carrier material. Any suitable mark or dye that will identify or color the bibulous material and thus distinguish the "handling zone" from the reagent impregnated zones may be used. For example, it has been found that about 0.40 to 0.60 grams of a dye dissolved in a suitable solvent, and adjusted to 100 ml may be applied to the bibulous carrier material. The preferred dye solution contains 0.50 grams FD & C Blue No. 2, 0.10 grams FD & C Red No. 2 and 0.10 grams of water soluble Nigrosin. However, other dye solutions could be used with equal effectiveness.

Bibulous carrier materials which are suitable for use in the practice of this invention are those materials which, by means of capillary action, have been found to hold liquid. Such materials include filter paper, felt, porous ceramic strips, woven or matted fiber and the like. A particularly preferred bibulous material is heavy weight filter paper.

In preparing the diagnostic test system of this invention, a roll or suitable bibulous material, for example, a 10 meter roll of filter paper, may be used. The substrate solution, the buffer solution and the barrier solution are applied to the entire roll lengthwise, in parallel zones or bands, by passing the filter paper between size applicator rollers which pick up the reagent solution from reservoirs. The filter paper becomes impregnated with the solution as it passes over the rollers. The amount of reagent deposited on the appropriate zone of the filter paper is a function of the size of the applicator and the number of times the filter paper is passed over the applicator roller. Additionally, both sides of the filter paper may be coated, if desired. After all reagent solutions have been applied to appropriate zones of the filter paper roll and evaporated to dryness, the filter paper is cut into individual strips representing one test unit of the diagnostic test system of this invention, each of which contains sufficient quantities of substrate and buffer necessary for identification and differentiation of β-galactosidase-producing micro-organisms.

In use, one test unit or test strip of the diagnostic test system of this invention is inserted into a test tube containing a saline suspension of the unknown culture to be tested, with the substrate and buffer zones immersed in the test suspension. The tube is incubated at approximately 35°–37°C for about four hours and observed for the presence of yellow coloration in the liquid which is a positive indication of the presence of β-galactosidase-producing organisms. If the suspension remains colorless, the test is negative.

In order to further illustrate this invention the following examples are provided:

EXAMPLE I

Preparation of the Substrate Solution 70 ml of Acetone and 30 ml of distilled water are mixed and 5 grams of o-nitrophenyl-β-D-galactopyranoside is added, with stirring to dissolve the substrate.

EXAMPLE II

Preparation of the Buffer Solution 2.006 Grams of monobasic potassium phosphate and 12.106 grams of dibasic sodium phosphate are added to distilled water, brought to 100 ml, and warmed to about 60°C, with stirring to dissolve the buffer.

EXAMPLE III

Preparation of the Barrier Solution

Solution A 5.45 ml of Quilon C (duPont) solution is thoroughly mixed and added to 21.8 ml of isopropyl alcohol with constant stirring. 45.4 ml of water is added to the Quilon C/isopropyl alcohol solution. 27.3 ml of 0.05N sodium hydroxide is added with constant stirring and the entire solution is brought to 100 ml with distilled water.

Solution B 15 ml of Ethanol (95%) is added to 85 ml of Krylon 150 Crystal Clear and mixed thoroughly.

EXAMPLE IV

Preparation of the Identifying Dye Solution 0.50 Grams of FD & C Blue No. 2, 0.10 grams of FD & C Red No. 2 and 0.10 grams of water soluble Nigrosin are dissolved in distilled water and brought to 100 ml.

EXAMPLE V

Preparation of the Diagnostic Test System

A 10 meter roll of heavy weight filter paper 83 mm wide is used as the bibulous material. The substrate solution of Example I is placed in a reservoir from which it is fed onto the surface of a rotating applicator wheel. A 3.7 mm zone along the 10 meter edge of the filter paper is impregnated with the substrate solution by passing the filter paper over a rotating applicator wheel, having a width of 4 mm. The rotating wheel simultaneously advances the paper, and the coating is evaporated to dryness. This procedure is repeated 3 times, with drying between applications, on each side of the 3.7 mm substrate zone.

The buffer solution of Example II is placed in a reservoir and applied, by means of a rotating applicator wheel having a width of 4 mm to a 3.7 mm buffer zone contiguous to the substrate zone of the filter paper. The buffer solution is applied twice to each side of the buffer zone and allowed to dry after each application. The buffer zone must not overlap the substrate zone.

Barrier Solution A of Example III is placed in a reservoir and applied to the center of a 16 mm zone contiguous to the buffer zone by means of a rotating applicator wheel having a width of 5 mm. Application is made once to each side of this centered barrier zone. Barrier solution B of Example III is placed in a reservoir and applied over the impregnated solution A, without drying, on both sides of the entire 16 mm barrier zone by means of a rotating wheel having a width of 15 mm and allowed to dry.

The identifying dye solution of Example IV is placed in a reservoir and applied to a 6 mm zone along the 10 meter edge of the filter paper opposite the substrate zone by means of a 6.3 mm applicator wheel. The identifying dye solution is applied once to each side of the identifying zone and allowed to dry.

After all impregnated zones on the filter paper roll are thoroughly dry, the paper is cut along the 83 mm width into 6.3 mm strips.

EXAMPLE VI

Use of the Diagnostic Test System

A loopful of an unknown culture is suspended in 0.3 ml of saline in a 13 × 100 test tube. The diagnostic test strip of Example V is inserted so that the zone opposite the identifying dye zone is immersed, and incubated in a water bath for 4 hours at 35°–37°C. The development of a yellow coloration in the liquid indicates a positive test result. If the liquid remains colorless, the test is negative.

We claim:

1. A method for preparing a diagnostic test system for detecting the production of β-galactosidase by bacterial hydrolysis of an o-nitrophenyl-β-D-galactopyranoside substrate which comprises:

A. Preparing an aqueous solution containing from about 0.5% to about 5.0% weight/volume, based on the volume of the total solution, of o-nitrophenyl-β-D-galactopyranoside and from about 25% to about 75% by volume of acetone;

B. Preparing a solution of a buffer system, which will maintain a pH of from about 6.5 to about 8.5, containing from about 0.5 molar to about 1.0 molar buffer;

C. Applying substrate solution (A) to a zone of a bibulous material and evaporating to dryness to provide from about 0.05 mg to about 3.0 mg of o-nitrophenyl-β-D-galactopyranoside on one test unit of the bibulous material; and D. Applying the solution of buffer system (B) to a zone of the bibulous material separate from and contiguous to substrate zone (C) above and evaporating to dryness to provide from about 0.01 to about 0.1 millimoles of buffer on one test unit of the bibulous material.

2. A method according to claim 1 wherein a buffer system which will maintain a pH from about 7.2 to about 7.6 is used.

3. A method according to claim 2 wherein a monobasic potassium phosphate and dibasic sodium phosphate buffer system is used.

4. A method according to claim 2 wherein a waterproof barrier solution which is chemically inert in the diagnostic test system is prepared, applied to a zone of the bibulous material contiguous to the outer-most reagent impregnated zone, and evaporated to dryness.

5. A method according to claim 2 which comprises:
   A. Preparing an aqueous solution containing about 5.0% weight/volume, based on the volume of the total solution, of o-nitrophenyl-β-D-galactopyranoside and about 70% by volume of acetone;
   B. Preparing a solution of a buffer system, which will maintain a pH of about 7.4, containing about 1 molar buffer;
   C. Applying substrate solution (A) to a zone of a bibulous material and evaporating to dryness to provide about 1.5 mg of o-nitrophenyl-β-D-galactopyranoside on one test unit of the bibulous material; and
   D. Applying the solution of buffer system (B) to a zone of the bibulous material contiguous to substrate zone (C) above and evaporating to dryness to provide about 0.02 millimoles of buffer on one test unit of the bibulous material.

6. A method according to claim 5 wherein a monobasic potassium phosphate and dibasic sodium phosphate buffer system is used.

7. A method according to claim 6 wherein a waterproof barrier solution which is chemically inert in the diagnostic test system is prepared, applied to a zone of the bibulous material contiguous to the outer-most reagent impregnated zone, and evaporated to dryness.

8. A method according to claim 6 wherein an identifying dye solution in prepared, applied to an extremity of the bibulous material opposite the reagent impregnated zones, and evaporated to dryness.

9. A diagnostic test system for detecting the production of β-galactosidase which comprises a bibulous material having on one test unit:
   A. A substrate zone containing from 0.05 mg to about 3.0 mg of dry o-nitrophenyl-β-D-galactopyranoside;
   B. A buffer zone separate from and contiguous to the substrate zone of (A), containing from about 0.01 to about 0.1 millimoles of a dry buffer system which will maintain a pH of from about 6.5 to 8.5.

10. A diagnostic test system according to claim 9 wherein the buffer system maintains a pH of from about 7.2 to about 7.6.

11. A diagnostic test system according to claim 10 wherein a monobasic potassium phosphate and dibasic sodium phosphate buffer system is used.

12. A diagnostic test system according to claim 10 wherein a dry waterproof barrier zone, which is chemically inert in the diagnostic test system is present, contiguous to the outer-most reagent impregnated zone.

13. A diagnostic test system according to claim 9 wherein the substrate zone of the bibulous material contains about 1.5 mg of dry o-nitrophenyl-β-D-galactopyranoside and the buffer zone contains about 0.02 millimoles of buffer which maintains a pH of about 7.4.

14. A diagnostic test system according to claim 13 wherein a monobasic potassium phosphate and dibasic sodium phosphate buffer system is used.

15. A diagnostic test system according to claim 13 wherein a dry waterproof barrier zone, which is chemically inert in the diagnostic test system is present, contiguous to the outer-most reagent impregnated zone.

16. A diagnostic test system according to claim 15 wherein a dry identifying dye zone is present on the extremity of the bibulous material opposite the reagent impregnated zone.

17. A method for identifying and differentiating micro-organisms which produce β-galactosidase which comprises:
   A. Immersing the substrate and buffer zones of the diagnostic test system of claim 9 in a test tube containing about 0.3 ml of a saline suspension of an unknown culture;
   B. Incubating the test tube of (A) for about four hours at from about 35°C to about 37°C; and
   C. Observing the liquid in the test tube of (B) for the presence of yellow coloration as a positive indication that β-galactosidase-producing micro-organisms are present.

* * * * *